US012645687B2

(12) United States Patent (10) Patent No.: US 12,645,687 B2

MacClary et al. (45) Date of Patent: *Jun. 2, 2026

(54) SYSTEM AND METHOD FOR QUERY MANAGEMENT AND EDUCATION

(71) Applicant: Artifact Health, Inc., Boulder, CO (US)

(72) Inventors: Marisa MacClary, Lexington, ME (US); Meir Gottlieb, Nederland, CO (US)

(73) Assignee: Artifact Health, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/801,017

(22) Filed: Aug. 12, 2024

(65) Prior Publication Data

US 2025/0045283 A1 Feb. 6, 2025

Related U.S. Application Data

(63) Continuation of application No. 18/335,842, filed on Jun. 15, 2023, now Pat. No. 12,099,511, which is a (Continued)

(51) Int. Cl.
*G06F 16/2458* (2019.01)
*G06F 16/27* (2019.01)

(Continued)

(52) U.S. Cl.
CPC .......... *G06F 16/2471* (2019.01); *G06F 16/27* (2019.01); *G06Q 40/08* (2013.01); *G16H 10/60* (2018.01)

(58) Field of Classification Search
CPC ..... G06F 16/2471; G06F 16/27; G06Q 40/08; G16H 10/60

(Continued)

(56) References Cited

U.S. PATENT DOCUMENTS

2013/0162424 A1* 6/2013 Treacy ................... G16H 40/20
340/502
2014/0330577 A1* 11/2014 Herman ................. G16H 40/67
705/2
2016/0012186 A1* 1/2016 Zasowski ............... G16H 10/60
705/3

FOREIGN PATENT DOCUMENTS

AU 2014223375 B2 * 5/2017 ............. G06F 16/93

OTHER PUBLICATIONS

Chapman, Improving The Query Process, Apr. 2013, For The Record, vol. 25 No. 6, fortherecordmag.com/archives/0413p22. shtml, p. 22 (Year: 2013).*

* cited by examiner

*Primary Examiner* — Joy Chng

(74) *Attorney, Agent, or Firm* — Sprinkle IP Law Group

(57) ABSTRACT

A cloud-based, query management and education system enables provider organizations to query and educate clinicians on how to clarify clinical documentation, resulting in more accurate reimbursement, public reporting, research and policy decisions. Query authors create compliant queries from stored templates which may be supplemented by attaching and/or annotating selected documentation from the patient record. Clinician responses to such queries automatically generate addenda in the relevant patient record. All events around a query are tracked and reportable through a graphical performance scorecards and reporting dashboards.

20 Claims, 10 Drawing Sheets

Related U.S. Application Data continuation of application No. 17/684,960, filed on Mar. 2, 2022, now Pat. No. 11,720,582, which is a continuation of application No. 15/369,359, filed on Dec. 5, 2016, now Pat. No. 11,309,067.

(60) Provisional application No. 62/262,936, filed on Dec. 4, 2015.

(51) Int. Cl.
*G06Q 40/08*        (2012.01)
*G16H 10/60*        (2018.01)

(58) Field of Classification Search
USPC ........................................................ 705/2–3
See application file for complete search history.

QUERY VIEW

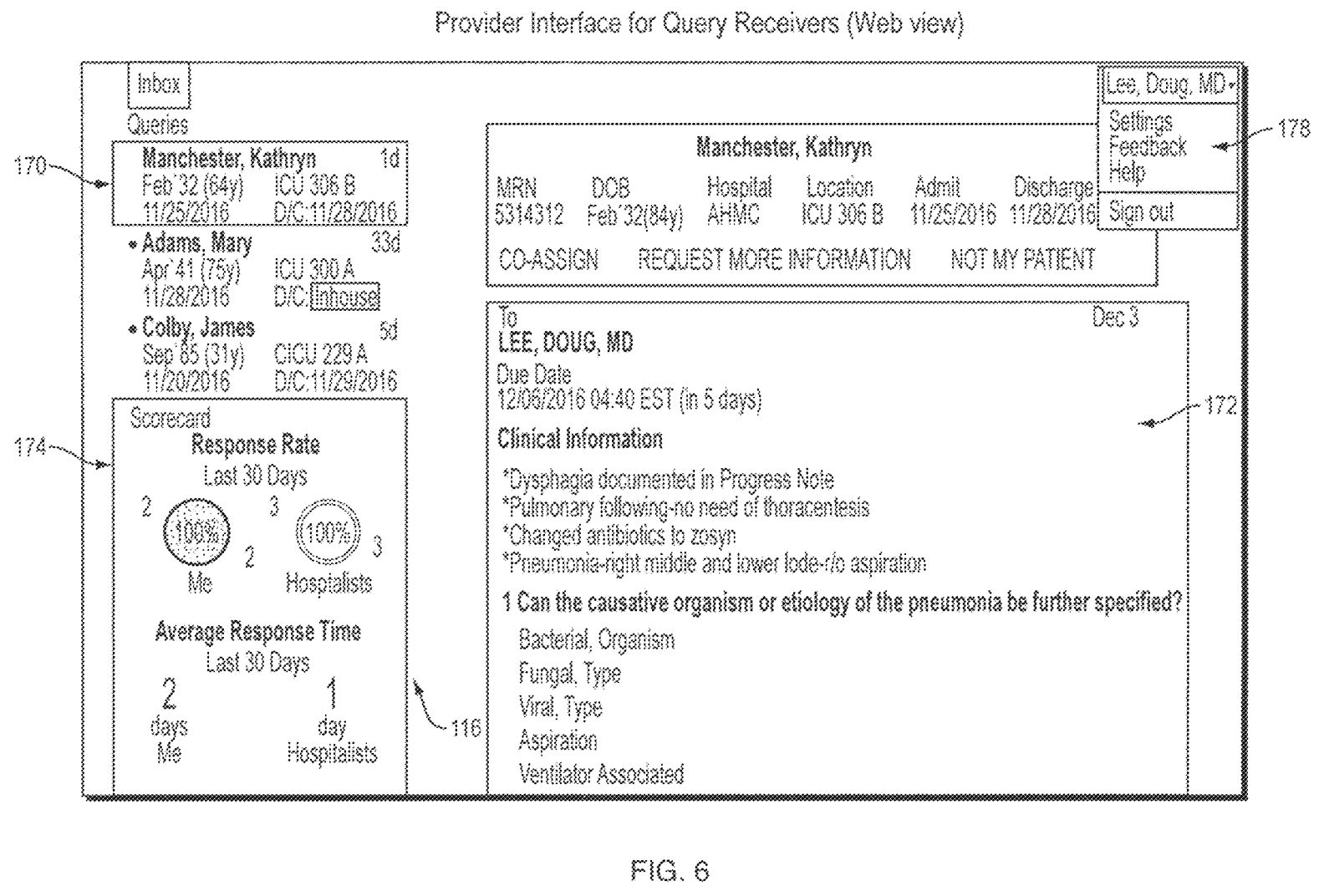

Provider Interface for Query Receivers (Web view)

Lee, Doug, MD▾

Settings
Feedback
Help
Sign out

Inbox
Queries

Manchester, Kathryn                    1d
Feb 32 (64y)    ICU 306 B
11/25/2016    D/C:11/28/2016    33d ● Adams, Mary
Apr 41 (75y)    ICU 300 A
11/28/2016    D/C: Inhouse    5d ● Colby, James
Sep 05 (31y)    CICU 229 A
11/20/2016    D/C:11/29/2016

Manchester, Kathryn

MRN        DOB            Hospital    Location        Admit            Discharge
5314312    Feb 32 (84y)    AHMC        ICU 306 B        11/25/2016        11/28/2016

CO-ASSIGN    REQUEST MORE INFORMATION        NOT MY PATIENT

To                                                                        Dec 3
LEE, DOUG, MD
Due Date
12/06/2016 04:40 EST (in 5 days)

Clinical Information

*Dysphagia documented in Progress Note
*Pulmonary following-no need of thoracentesis
*Changed antibiotics to zosyn
*Pneumonia-right middle and lower lode-/o aspiration 1 Can the causative organism or etiology of the pneumonia be further specified?

Bacterial, Organism
Fungal, Type
Viral, Type
Aspiration
Ventilator Associated

Scorecard

Response Rate
Last 30 Days
3

(100%)                    (100%)
2    2                    Hospitalists
days
Me

Average Response Time
Last 30 Days 2                        1
days                    day
Me                      Hospitalists

FIG. 6

Query Platform, 102

Manager Interface, 114
Provider Interface, 116
Template Editor, 120
Publisher Interface, 122
Reports, 124
Query Author Resources, 126
Consultant Interface, 128

Database, 108

NETWORK, 112

DEVICE, 106

DATA STORE, 110

USER COMPUTING DEVICE, 104

100

SYSTEM AND METHOD FOR QUERY MANAGEMENT AND EDUCATION

CROSS-REFERENCE TO RELATED APPLICATION(S)

This application is a continuation of, and claims a benefit of priority under 35 U.S.C. 120 from, U.S. patent application Ser. No. 18/335,842 filed Jun. 15, 2023, issued as U.S. Pat. No. 12,099,511, entitled "SYSTEM AND METHOD FOR QUERY MANAGEMENT AND EDUCATION," which is a continuation of, and claims a benefit of priority under 35 U.S.C. 120 from, U.S. patent application Ser. No. 17/684,960 filed Mar. 2, 2022, issued as U.S. Pat. No. 11,720,582, entitled "SYSTEM AND METHOD FOR QUERY MANAGEMENT AND EDUCATION," which is a continuation of, and claims a benefit of priority under 35 U.S.C. 120 from, U.S. patent application Ser. No. 15/369,359 filed Dec. 5, 2016, issued as U.S. Pat. No. 11,309,067, entitled "SYSTEM AND METHOD FOR QUERY MANAGEMENT AND EDUCATION," which claims a benefit of priority under 35 U.S.C. § 119(e) from U.S. Provisional Application No. 62/292,936 filed Dec. 4, 2015. All applications listed in this paragraph are fully incorporated by reference herein for all purposes.

FIELD OF THE INVENTION

The disclosure relates cloud-based, query management and education system, and, more specifically, to a system and method which enables greater clarity in clinical documentation.

BACKGROUND OF THE INVENTION

On average, 30% of all hospital inpatient medical records have a query opportunity, which means an opportunity to ask clinicians to go back to the patient chart and clarify their documentation of the patient's diagnoses and/or treatment. This percentage increased at the end of 2015 with the introduction of ICD-10, a new diagnostic code set upon which reimbursement is based, because ICD-10 requires greater documentation specificity to support optimal reimbursement and accurate quality reporting. Because clarifying documentation is directly linked to proper reimbursement and accurate quality reporting, it's critical to the financial survival of provider organizations that clinicians respond to documentation-related queries.

Across U.S. hospitals, over 40% of documentation-related queries are communicated to clinicians on paper and the majority of the remainder via faxes or email. Clinicians receive queries from multiple groups employed by the provider organization ("query authors") who typically work in silos with little to no coordination on queries. This results in the clinician receiving more queries than necessary and an unorganized query process difficult for the clinician to manage and prioritize.

Query authors are responsible for reviewing documentation and assigning the most accurate clinical codes to the patient chart for reimbursement and reporting purposes. They ask clinicians to respond to a query by going back into the patient chart and updating the patient's documentation or by responding directly on a query form, which often becomes part of the legal medical record. The updated documentation substantiates a more accurate clinical code. Because the query process is not automatically tracked, it's difficult for query authors to know when and where the clinician responded within the patient record. Provider organizations are largely frustrated by the overall lack of reporting capabilities and accountability in the physician query process.

It is also difficult for query authors to find opportunities to train and educate clinicians on how to avoid queries. They often create paper fliers, posters, pamphlets and hold lunch sessions to communicate information about documentation best practices.

Clinicians report that it can take 15-20 minutes to respond to one query. Overall, they describe the process as burdensome and outside of patient care responsibilities. Because of the clinician-unfriendly nature of the process, many queries go unanswered driving query response rates down and contributing to already enormous financial pressures facing provider organizations.

Currently, there are no stand-alone electronic query platform 102$s$ on the market. Also, there are no mobile query workflows built within existing coding applications or electronic medical records systems or systems that bring together all groups that query the clinician in a collaborative way creating maximum coordination, visibility and accountability. Finally, no singular product on the market is delivering queries to clinicians with a simple one-step response workflow.

Accordingly, the need exists for a standardized query review and response workflow on a mobile device that is easy and fast for clinicians and allows them to handle increasing query volume.

A further need exists for a collaborative approach to the query management process that introduces full visibility into the query process and brings together all types of query authors associated with a provider organization to coordinate on documentation-related queries.

Yet, a further need exists for a query process that allows provider organizations to purchase or create their own compliant query templates and share them across the organization in a standardized way.

SUMMARY OF THE INVENTION

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIG. 6 illustrates conceptually a Provider Interface for Query Receivers (Web view) in accordance with the disclosure;

DETAILED DESCRIPTION

Figure 1:
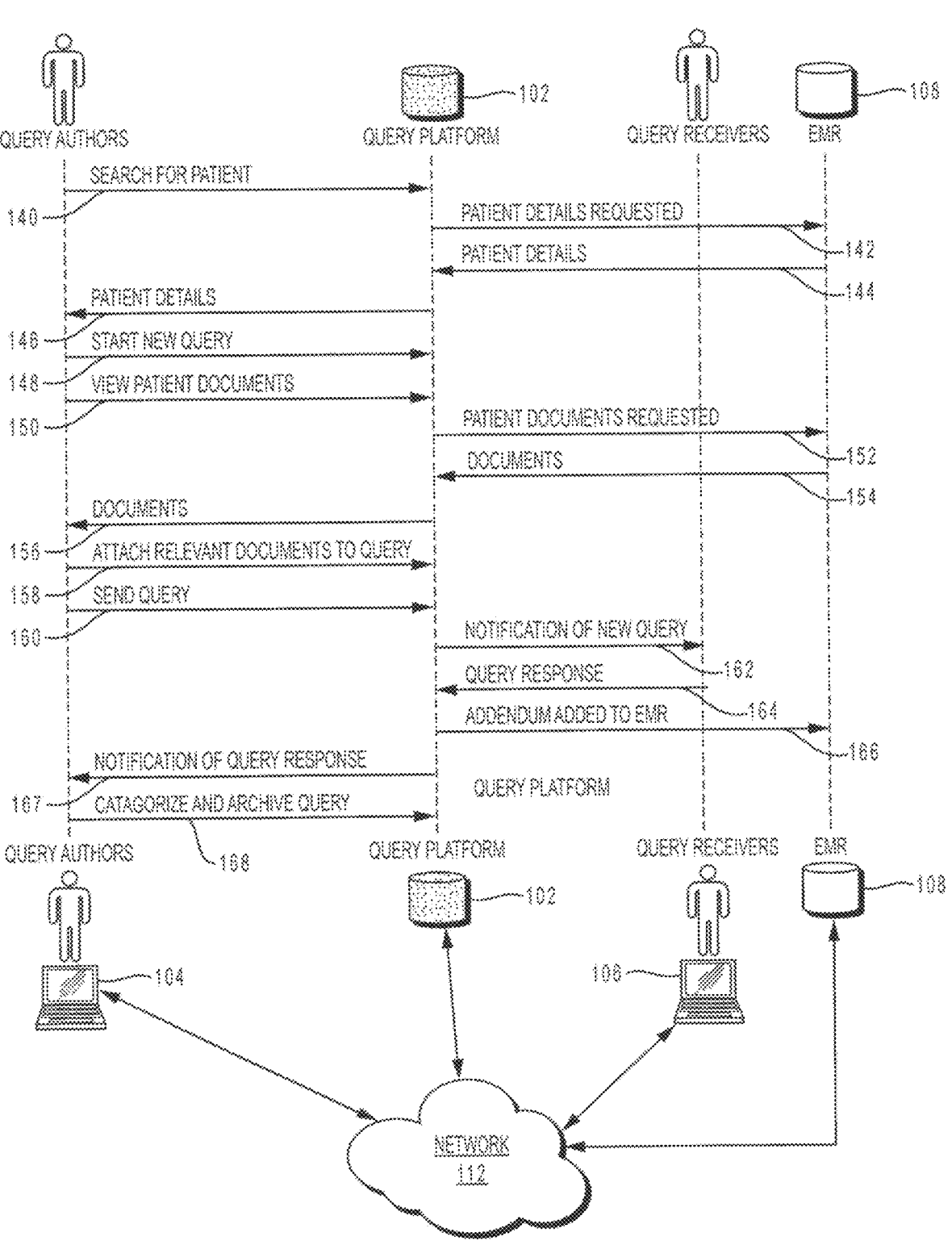
FIG. 1 illustrates conceptually a workflow chart displaying the query platform 102 process and interfaces to the electronic medical record in accordance with the disclosure.

The present disclosure will be more completely understood through the following description, which should be read in conjunction with the drawings. In this description, like numbers refer to similar elements within various embodiments of the present disclosure. The skilled artisan will readily appreciate that the methods, apparatus and systems described herein are merely exemplary and that variations can be made without departing from the spirit and scope of the disclosure.

Disclosed is a cloud-based, query management and education system 100, referred to herein as query platform 102 which provider organizations can query and educate clinicians on how to clarify clinical documentation, thereby resulting in more accurate reimbursement, public reporting, research and policy decisions.

Referring to the figures, an embodiment of a system 100 comprises a query platform 102, in communication with one or more computing devices 104 and 106, which may behave as either query authors or query receivers, as explained herein, and one or more a databases 108 or data store 110, any of which may be interconnected via a private and/or public network topology 112. In the illustrative embodiment, query authors may utilize computing device 104 while query receivers may utilize computing device 106.

Query Platform

The query platform 102 can be used across any healthcare provider organization network that submits coded clinical data for reimbursement and reporting purposes. The query platform 102 can also be used in other non-healthcare settings where one group must query another group and track, share and report on queries, events around queries and query responses.

In an illustrative embodiment of a healthcare provider organization, primary users of the query platform 102 may include any of clinicians, clinical documentation improvement specialists, medical coders, billers, quality staff, and hospital or practice management/administration. The query platform 102 facilitates compliant communication of documentation-related queries between query receivers (e.g., clinicians) and query authors (e.g. clinical documentation specialists, medical coders, quality staff, billers, etc.), as illustrated in FIG. 1.

The query platform 102 can be electronically interfaced to other system components for user login authentication, to retrieve patient registration and demographic data, to retrieve patient documents and images, and to export clinician responses to the official patient medical record. Also, the system workflow can be modified to operate without these interfaces in place.

In an illustrative embodiment, query platform 102 may comprise the following functional modules: Manager Interface 114, Provider Interface 116, Template Editor 120, Publisher Interface 122, Reporting 124, Query Author Resources 126, and Consultant Interface 128, as described in detail below. These functional modules may generate network accessible user interfaces through which query authors and query receivers may interact with query platform 102.

Manager Interface

Figure 2:
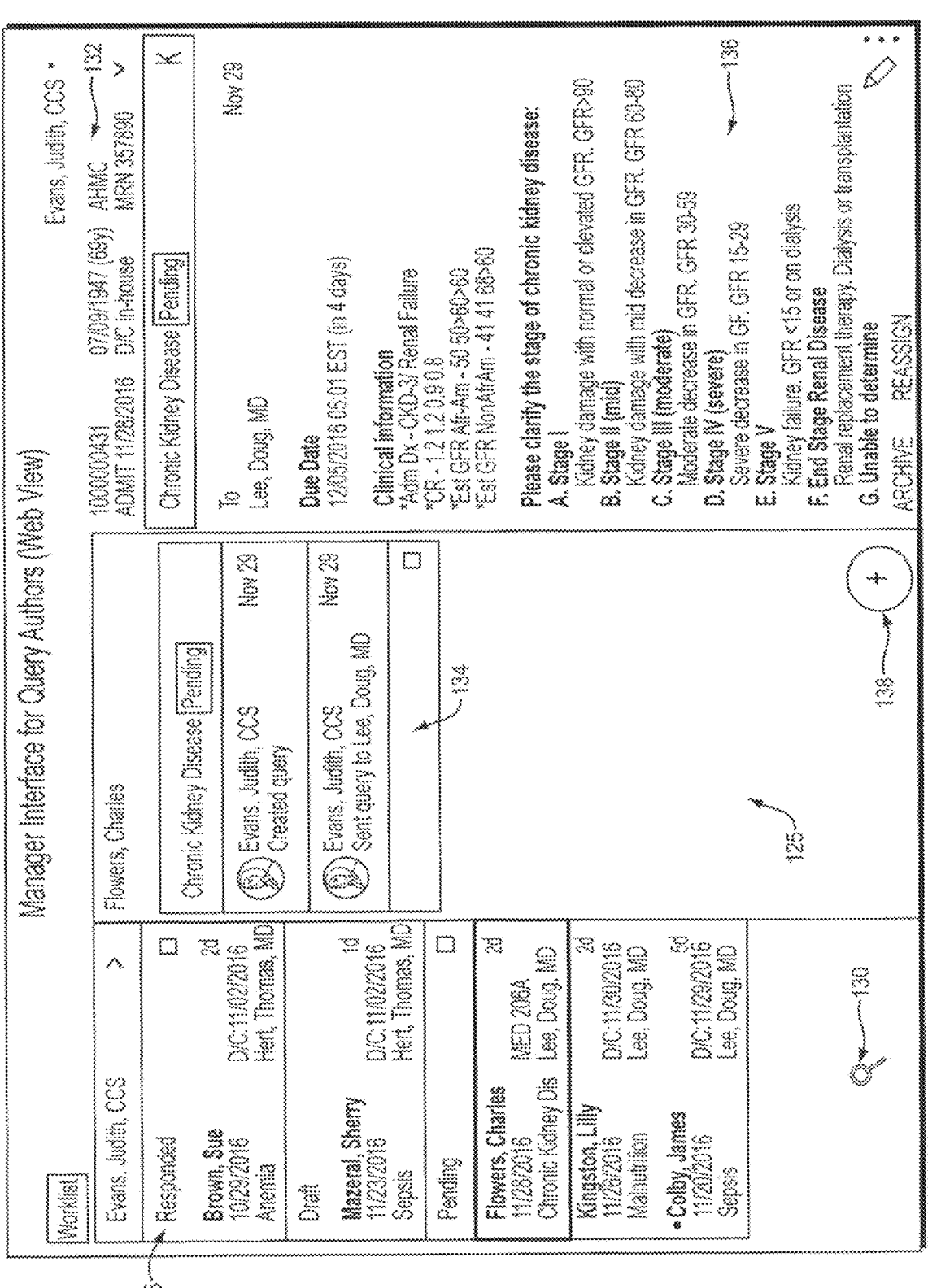
FIG. 2 illustrates conceptually a Manager Interface for Query Authors (Web view) in accordance with the disclosure.

The query platform 102 comprises a Manager Interface 114 that generates a network accessible user interface that enables Query authors to create queries. FIG. 2 illustrates conceptually a user interface 125 generated by the Manager interface module 114 as comprising the following sub-components: Patient Search 130, Patient Banner 132, Query Activity Feed 134, Query View 136 and Work List 135.

Referring to FIGS. 1 and 2, query authors can create queries by searching for patients by encounter number or medical record number using the Patient Search dialog box 130 in the upper left corner of user interface 125. From the search results, the query author may review all encounters for a patient by date of admission, date of discharge, if available, medical record number and the number of queries that exist on the encounter. When an encounter is selected, full patient demographic information is displayed across the top of the user interface 125 in the Patient Banner section 132 including any of name, date of admission, date of discharge if available, date of birth, age, location, account number or billing number, medical record number, length of stay, days post discharge if available, and insurance company. Any of the foregoing patient data displayed in the Patient Banner section 132 may be stored in memory associated with system 100, including the data store 110 and/or database 108. Any queries that exist on the selected encounter and their histories are displayed in the center Query Activity Feed section 134. The query author may click into the Query Activity Feed section 134 on a specific query thread to open the full Query View section 136 in the right pane. The foregoing activities are illustrated conceptually by communication transmissions 140, 142, 144, and 146, as illustrated in FIG. 1.

After the query author selects the appropriate patient and encounter, he or she may create a new query to send to a clinician. The query author selects the create a query command graphic 138 to initiate a new query and can then select the appropriate clinician(s) from a directory of clinician names uploaded from the provider organization to direct the query. The query platform 102 can suggest a list of possible clinicians that have documented on the patient for selection and also allows the query author to type in portions of a clinician's first or last name for a full search of the directory. Next, the query author selects a pre-defined query template from a template library or a free-text template associated with query platform 102 to create their own query. The template library is created through the Template Editor 120, described further below.

With the selected template displayed in the Query View 136, the query author may edit the query question, apply customizable tags for reporting purposes, manually enter or paste-in clinical indicators from other systems, attach supporting documentation interfaced from other systems and annotate areas within the supporting documentation to direct the clinician's attention. When the query is complete, the query author can click the "send" button to send the query to the clinician's Inbox within the query platform 102. The query displays the date and time the query was sent and a "due date" for the clinician to know when a response is required. The due date is automatically generated based on the provider organization's specific policy at the time the query is sent to the clinician. The foregoing activities are illustrated conceptually by communication transmissions 148, 150, 152, 154, 156, 158 and 160, as illustrated in FIG. 1.

The query platform 102 tracks all events and actions taken on a query chronologically in the center Query Activity Feed section 134. The Query Activity Feed 134 can be shared widely across all query authors or other configured groups of users. From the Query Activity Feed 134, users may click on query threads to open the full Query View 136 in the right pane. The Query Activity Feed 134 may comprise any of a brief description of the action taken; the date, time and age of the action; and the name, title and picture of the user who took the action on the query or posted the comment or conversation, or such data being maintained in a data structure associated with the query stored in system memory.

Query authors or other users of the Manager Interface 114 may post comments on queries in the Query Activity Feed 134 and direct those comments to other users of the Manager Interface 114. Notification of a comment appears in the Query Activity Feed 134. Users may also initiate new conversations on a patient encounter and direct conversations to other specific users.

A query author's Work List 135 displays all queries created or edited by the query author, the status of each query, and comments or conversations sent to or initiated by the query author, as illustrated in FIG. 2. Queries are displayed in the Work List 135 with their age from date sent to the clinician and are categorized by "responded", "pending", "draft", and "archived" status.

The Manager Interface 114 also allows query authors to send draft queries through a review process to ensure compliance. Queries that have been created but not yet sent to a clinician can be sent to a manager or supervisor for review. This process may be configurable so that it is available only to selected query authors whose queries need the additional review. The draft query appears in the manager's Work List 135 under a review category and can be edited and then sent on to the clinician by the manager. The query author views the status of the query from his or her Work List 135.

Answered queries are archived so that they are removed from the query author's "responded" section of the Work List 135 but retrievable in the future if necessary. When a clinician responds to a query, query authors read the response and before clicking "archive", may select customizable "tags" to describe the response for reporting on query activity and query impact. For example, query authors can indicate if the clinician agreed or disagreed with the query and if the query changed the DRG code, the severity of illness or the risk of mortality.

If the query platform 102 is interfaced with the patient medical record, as may be stored in system memory in any of devices 104 or 106, data store 110, database 108, or query platform 102, the clinician's response to the query, or the entire query with the response depending on how the provider organization has configured the query platform 102, automatically generates an addendum in the patient medical record at the time of the clinician's response or after a query author archives a query.

At any time, query authors may reassign pending queries to another clinician, often in cases where the original clinician has not responded by the due date. Clicking the "reassign" button allows the query author to carry forward the original query and select a new clinician. When the reassigned query is sent, the original query is archived and tracked as a "no response" for the original clinician, which impacts the clinician's query performance measures.

If a query response requires additional follow-up with the same clinician for further clarification, the query author may click the "reply" button to carry forward the original query, edit the query, and send a new query to the same clinician. The original query is archived and tracked as a "response" for the clinician. Finally, query authors can configure alerts to be sent to clinicians regarding pending queries at specific intervals. Alerts can be sent via email or by text message or push notification onto mobile devices. The foregoing activities are illustrated conceptually by communication transmissions 162, 164, 166, 167, and 168, as illustrated in FIG. 1.

Template Editor

Figure 10:
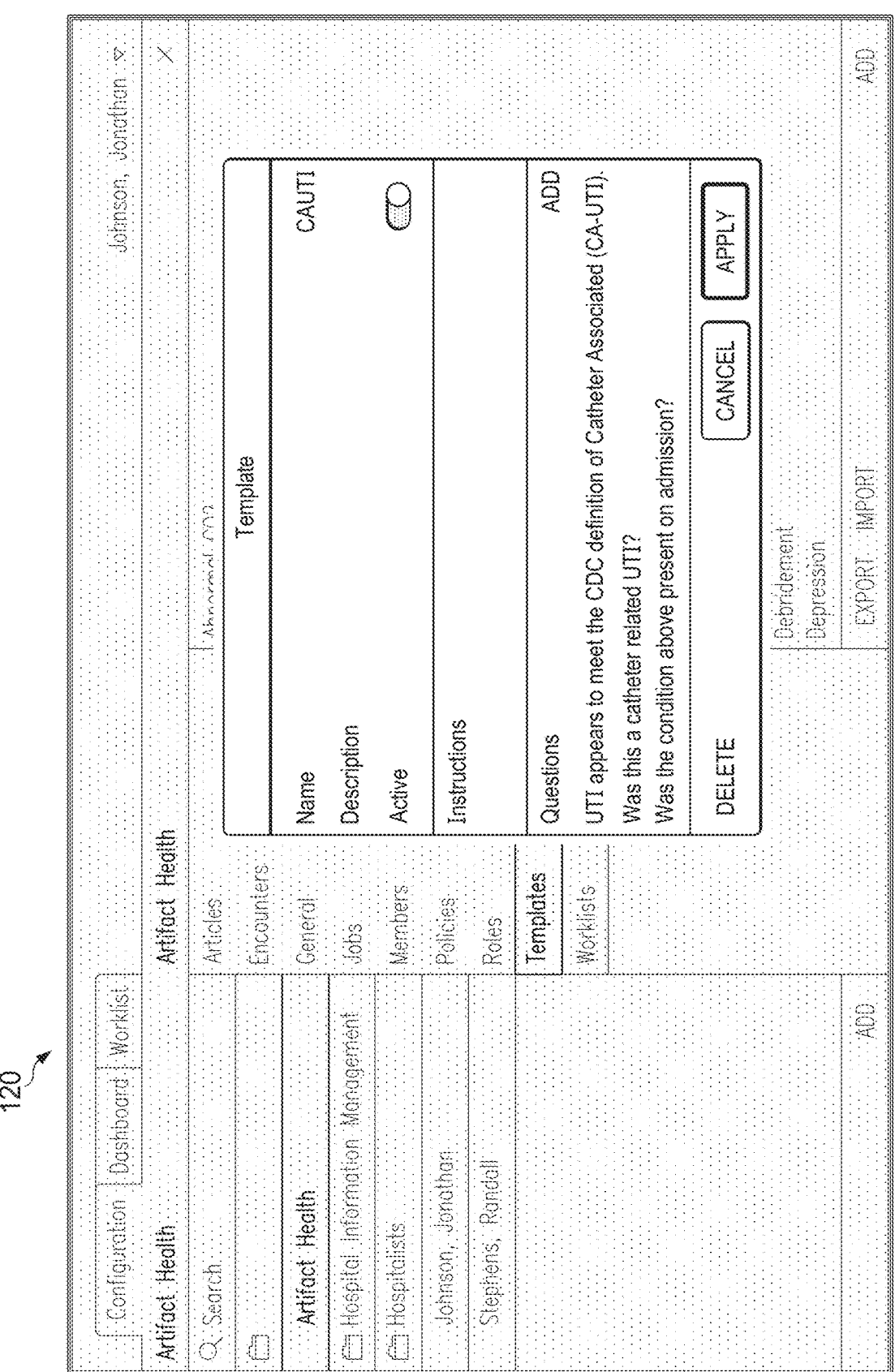
FIG. 10 illustrates conceptually a Template Editor for creating and maintain the query template library.

As illustrated in FIG. 10, a module which performs the functions of Template Editor 120, as described herein, may be part of the query platform 102. The Template Editor 120 generates a network accessible user interface that enables provider organizations to create, store and categorize an unlimited number of query templates, effectively enabling the creation of a template library. A query template may be implemented with a record or other data structure having data representing including any of the questions, a list of possible answers, clinical information which ultimately populate the patient's medical record, query title, query instructions, provider education tips, tags for reporting purposes and branding or footnote information. The Template Editor 120 enables provider organizations to continually edit and modify templates to keep them compliant and current and maintain version control of all templates.

FIG. 2 illustrates conceptually a Manager Interface for Query Authors in which the displays Patient Search 130 results, the Query Activity Feed 134 which tracks all events around a query and conversations, and the Query View 136 with a full view of a query with any of the following functionality: edit query, attach documentation, tag, send to clinician, reassign, reply, duplicate, revoke, delete a draft, spell check, archive and print. Note that the Patient Search 130 window section switches to the Work List 135 when a user/author is viewing or creating queries.

Provider Interface

The query platform 102 generates a network accessible user interface in the form of a Provider Interface 116 for query receivers, which in the healthcare provider organization embodiment would be for clinician users, as illustrated in FIGS. 3-6. The Provider Interface 116 may generate and display any of the following sections viewable on devices 104 or 106 including any of Query Inbox, Query View, Archive, Learning, Learning Archive, Scorecard, Meet the Team and Settings. The Query Inbox, Archive, Learning, Meet the Team and Settings sections may also function as links in the menu of the Provider interface for easy navigation 178.

Figure 3:
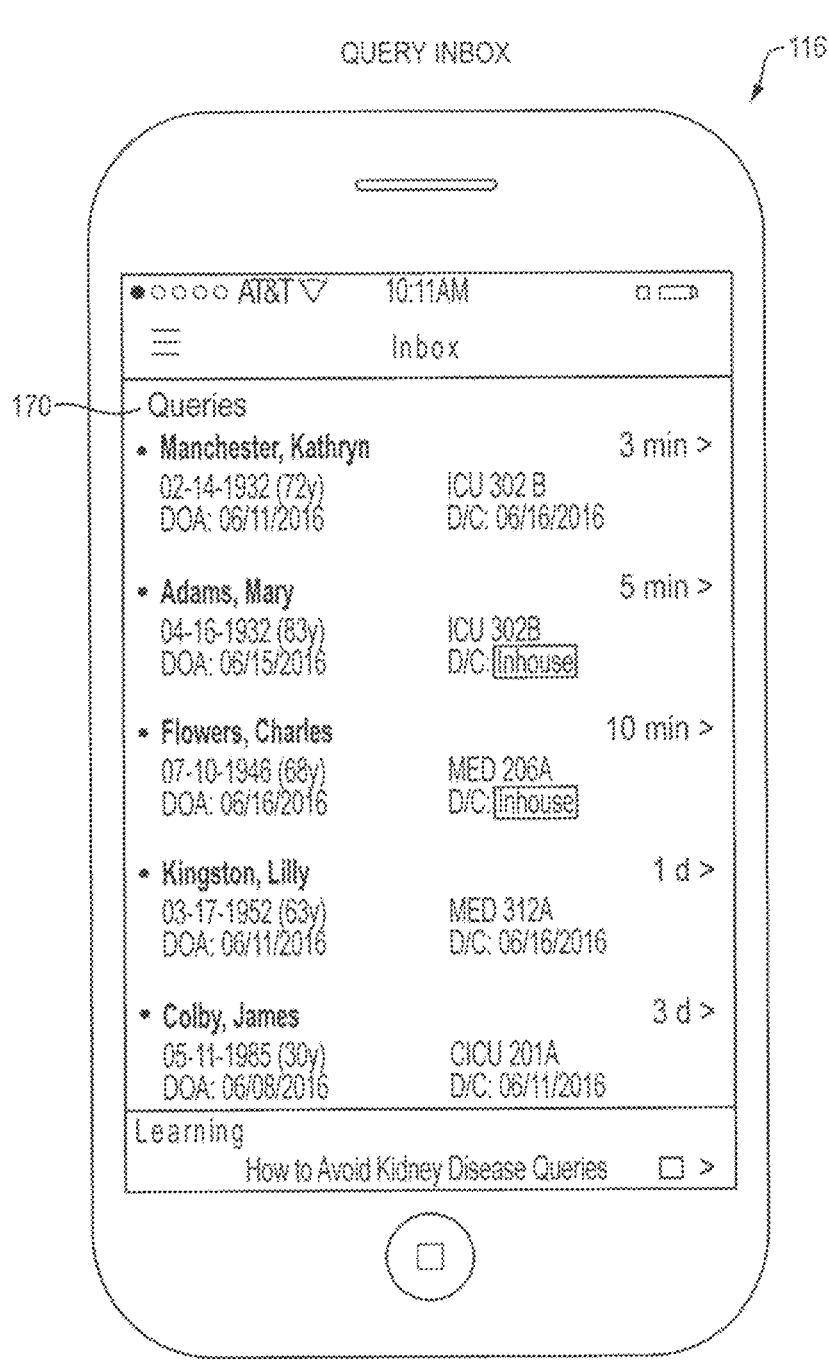
FIG. 3 illustrates conceptually a Provider Interface's Query Inbox (Mobile view) Listing of pending queries and their status for the clinician to respond to in accordance with the disclosure.

The Query Inbox 170 displays all pending queries for the clinician with status and patient identifying information, as illustrated in FIG. 3. A graphic icon, such as a blue dot indicates an unread query, well another graphic icon such as a red dot indicates a query approaching its due date as may be configured by the provider organization. The Inbox subsection may display queries with any of the following patient information: name, date of birth, age, date of admission, date of discharge if available, location, primary diagnosis, and query age.

A clinician may swipe left on any query in the Inbox subsection to select graphic icons, buttons, or other interface commands such as "remind me later" or "not my patient". Selecting a "remind me later" prompts the clinician to select a time from a menu of configurable options, which appear at the bottom of the application, to be reminded of the query. The query is then temporarily removed from the Inbox until the selected time. Selecting "not my patient" sends the query back to the query author and removes the query from the clinician's Inbox. Swiping right closes these buttons.

Figure 4:
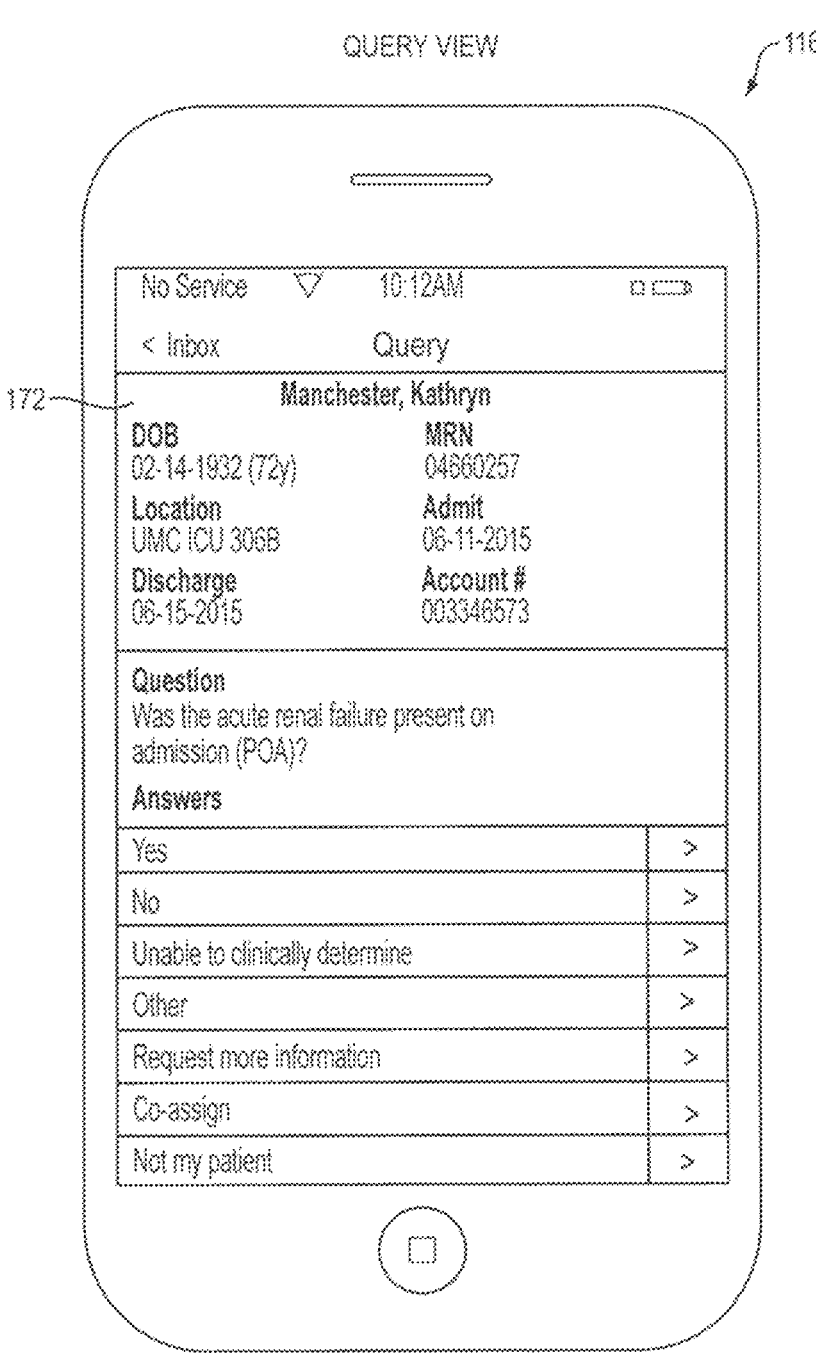
FIG. 4 illustrates conceptually a Provider Interface's Query View (Mobile view) in accordance with the disclosure.

A clinician may click on a query to open to the Query View 172, as illustrated in FIG. 4. The Query View 172 may display any of the data associated with a particular patient record including any of the following information: patient name; patient DOB; patient's last hospital location; date of admission; date of discharge if available; medical record number; account or encounter number; date query sent to clinician; requested response due date; query author name, title, email address and photograph; statement of the issue in the form of a question that does not lead or direct the clinician to document a specific response; a list of possible answers typically formatted as multiple choice, yes/no, or free-text; other standard answers including any of to that was one of is a "request more info", "co-assign" a query to another provider, "remind me later", and "not my patient"; provider education tip(s); name of the clinician(s) to whom the query is addressed; clinical indicators and other information entered by the query author; and attached documentation or snippets of documentation from the patient medical record or other interfaced external sources.

Clinicians can take action on the query from the Query View 172. Clicking on an answer to the question. The clinician may execute the addendum by clicking the "sign" button. Clinicians may also select the "X" to close any open view.

In addition to the query answers, the clinician may select a standard answer including any of "request more information", "co-assign", "not my patient", "remind me later". "Not my patient" and "remind me later" function as described above. "Request more information" gives the clinician the ability to type or use voice recognition to enter information to be communicated back to the query author. Then, clicking the "send" button removes the query from the Inbox and sends the response to the query author. The query author views the response, archives the query and may initiate a follow-up query with the additional information addressing the clinician's response.

If the clinician clicks "co-assign", the query platform 102 displays a list of suggested clinicians who have documented previously on the patient from which the clinician may select to co-assign the query. The clinician may also search the directory for a clinician to select for co-assignment. When the clinician selects a clinician to co-assign the query, the query is sent to the co-assignee's Inbox and also remains on the original clinician's Inbox until the query is answered by either clinician or removed by the query author. The original clinician's Inbox displays the name of the co-assignee under the patient information. Clinicians have an unlimited ability to continue to co-assign a query to additional clinicians until the query is answered or removed by the query author.

Clinician performance tracking can be configured in any way to impact clinicians on a co-assigned query. For example, if the co-assignee answers the query, credit can be given to both the original clinician and the co-assignee. All answered or removed queries can be viewed from the Archive section of the Provider Interface.

Figure 5:
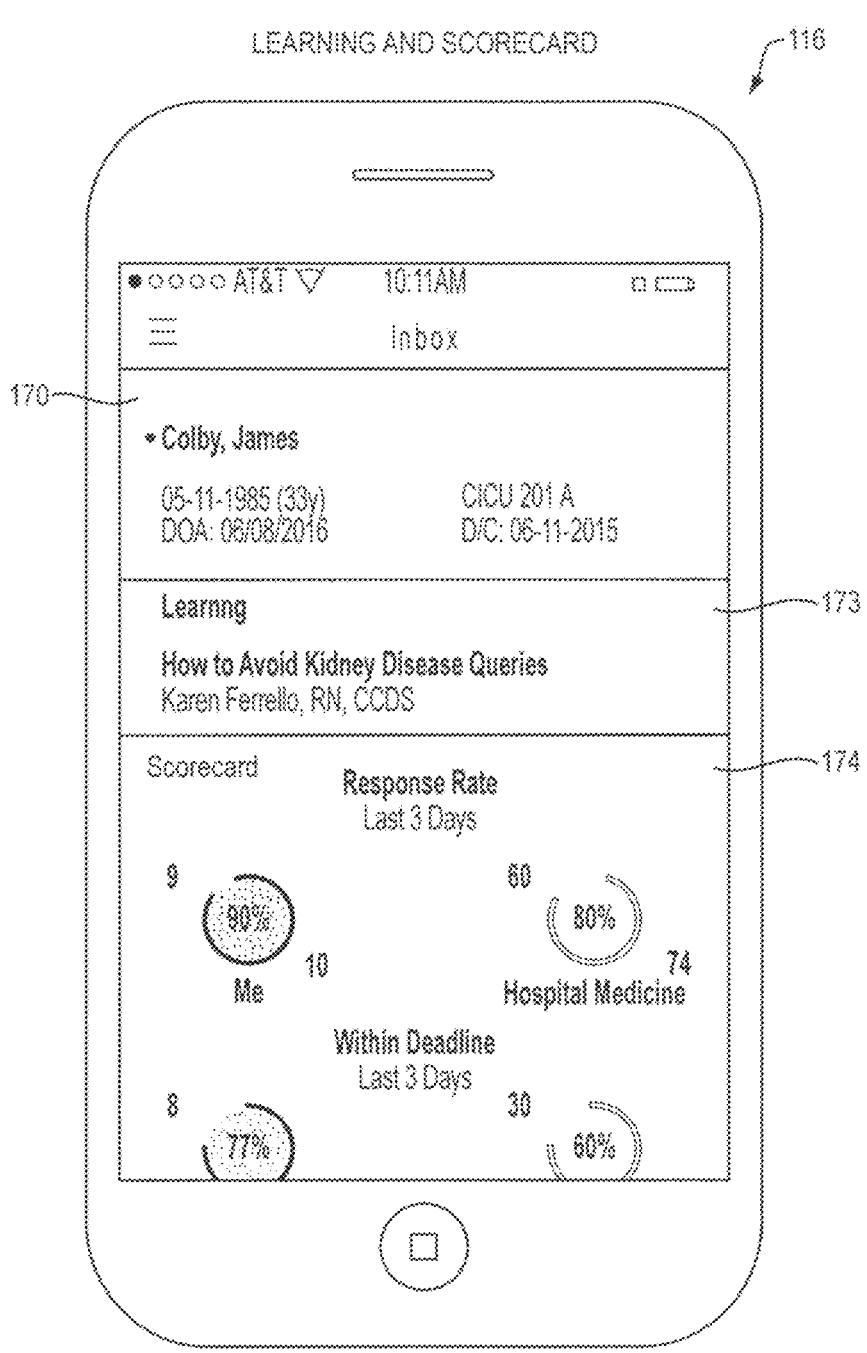
FIG. 5 illustrates conceptually a Learning and Scorecard (Mobile view) in accordance with the disclosure.

FIG. 5 illustrates conceptually a Learning 173 and Scorecard 174 sections. The Learning section enables targeted provider education to help reduce need for future queries to the clinician. The Scorecard section tracks and displays two important clinician performance measures, response rate and average time to respond. Scrolling down from the Inbox 170 reveals Learning interface 173 and Scorecard interface 174, as illustrated in FIG. 5. Learning interface 173 contains educational content uploaded to the Provider Interface 116 from the Publisher Interface 122, described below. Scorecard 174 graphically displays a clinician's real-time performance metrics as compared to his or her group as configured by the provider organization. The Scorecard 174 can be configured to track and display any metric(s) that the provider organization deems important to drive the desired outcomes for the query platform 102.

Finally, the Meet the Team and Settings areas are accessible via the menu in the Provider Interface 116. Meet the Team can be configured to display any of the name, title, email address and photograph of all query authors associated with that clinician or clinician's group. The Settings area gives the clinician options for customizing his or her Provider Interface such as any of enabling touch ID on a mobile device and enabling email, text message or push notifications on a mobile device to receive alerts about queries from query authors executed from the Manager Interface.

Publisher Interface

The query platform 102 generates a network accessible user interface in the form of a Publisher Interface 122 that enables provider organizations to upload any type of content to the Learning area 173 to assist clinicians in responding to queries. When clinicians click on a content topic to view it, the Provider Interface 116 then removes the content from the Learning area 173 and places it under Learning Archive. Using the Publisher Interface 122, content from the Learning area can be formatted as text, images and/or video. The Publisher Interface 122 allows authorized users to select specific individuals or groups to send content, configure dates for content to appear and disappear from clinician Provider Interfaces, and archive draft or expired content. The Publisher Interface 122 also tracks individual view counts for reporting purposes.

Reports

Figure 8:
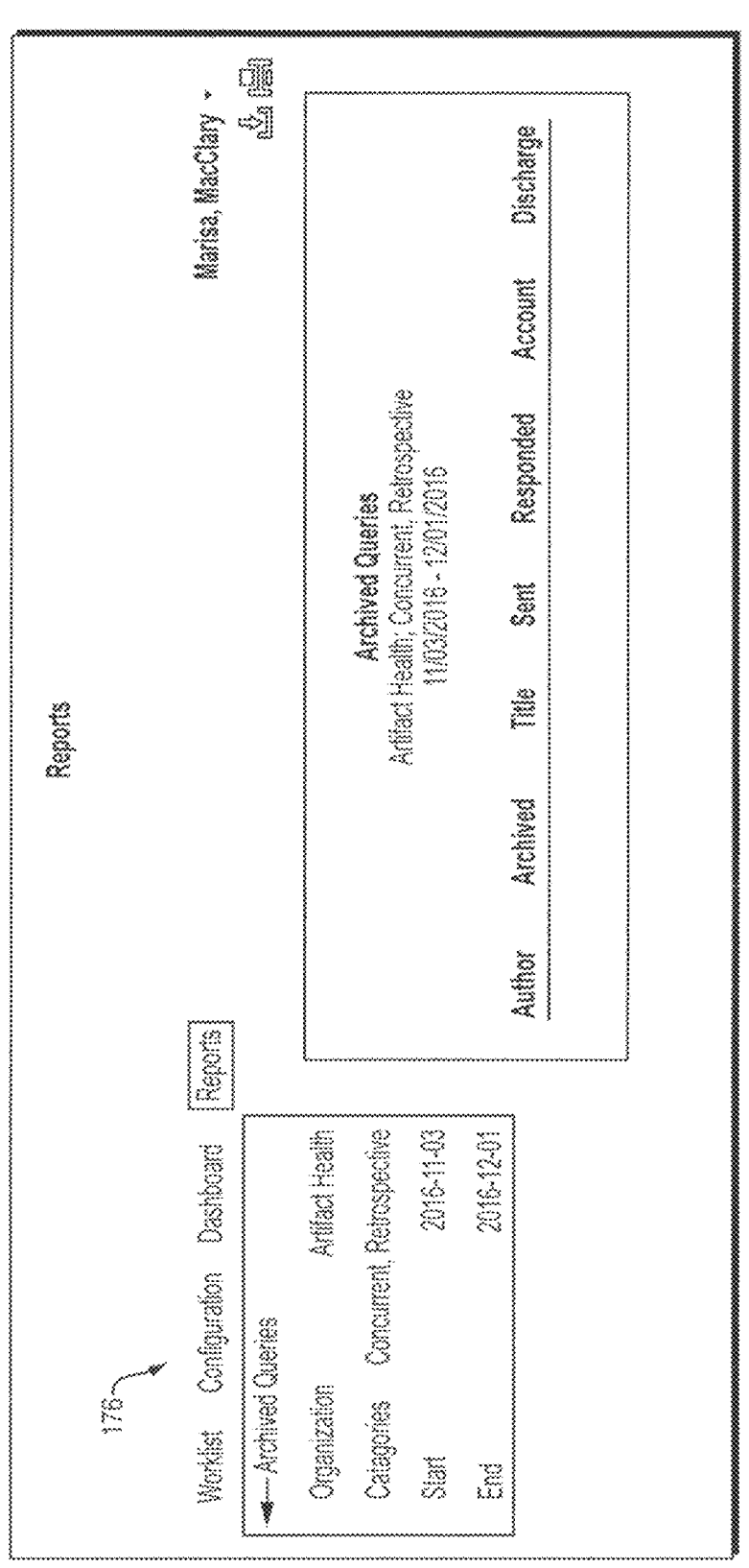
FIG. 8 illustrates conceptually a Report for tracking query activity metrics.
Figure 9:
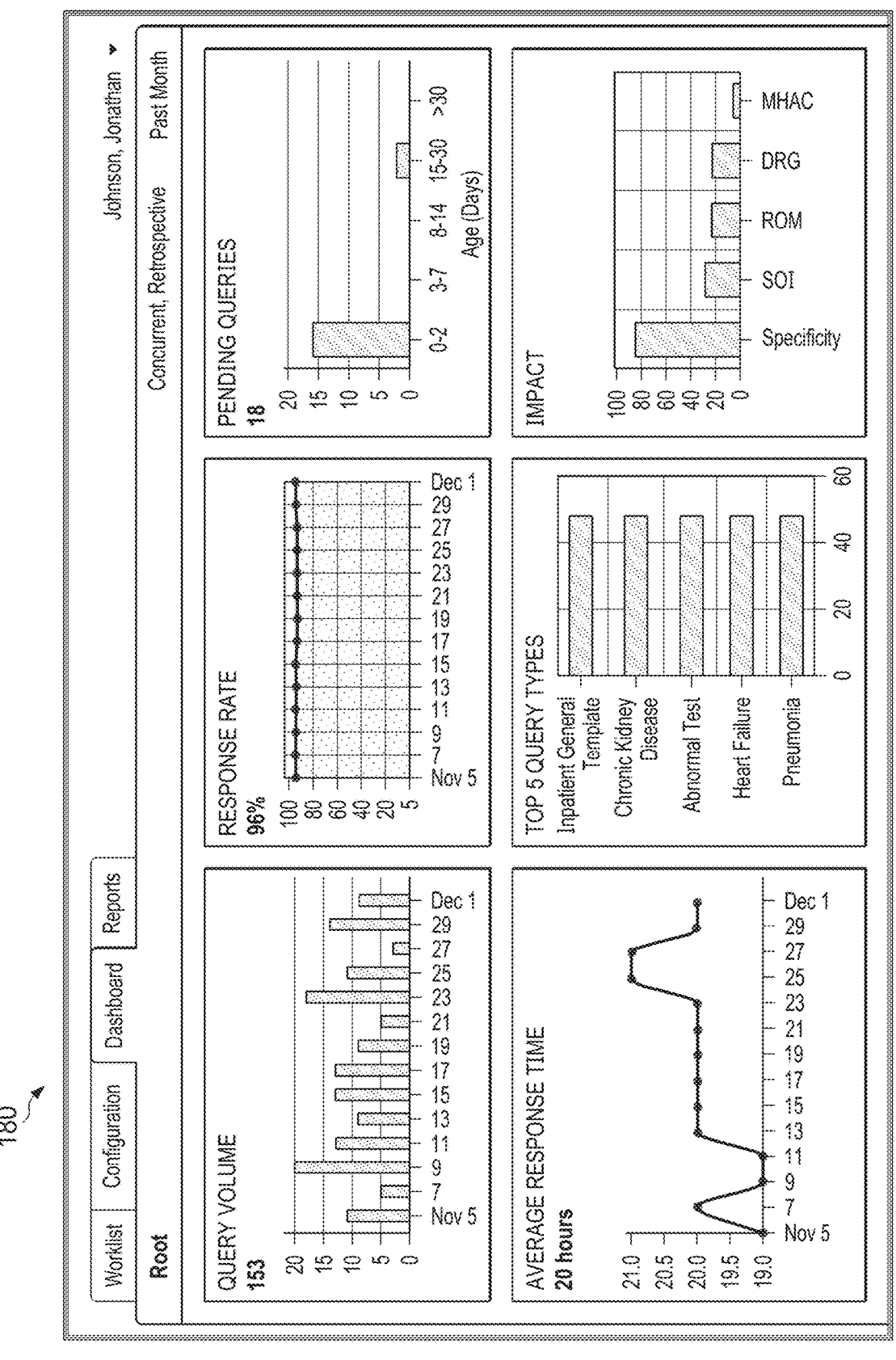
FIG. 9 illustrates conceptually a Report Dashboard for displaying query activity metrics.

As illustrated in FIGS. 8 and 9, the query platform 102 generates a network accessible user interface in the form of Reports 176 and dashboards 180 which track key metrics and allow users to run standard reports. Examples of standard reportable metrics include: query volume, query response rate, within deadline rate, query agreement rate, query impact and query type.

Query Author Resources

The query platform 102 generates a network accessible user interface in the form of a Query Author Resources area 126. Which exists within the Manager Interface 114 and provides a place for all query authors to post and share information and participate in conversations through a message board feature. Information may include educational content, hospital policies and alerts, consultant training materials, coding clinics and other guidelines.

Consultant Interface

The query platform 102 generates a network accessible user interface in the form of The Consultant Interface 128 enabling authorized consultants to provider organizations to author, manage and maintain query templates and provider education. The Consultant Interface 128 gives users the ability to access areas of the query platform 102 on behalf of the provider organization. Consultancies also have access to Reports to assist provider organizations with running specific reports and analyzing data from the system.

Any of the functional logic described here in including, but not limited to, the Meet the Team, Learning Archive, Publisher Interface, Query Author Resources, and Consultant Interface functions may also be implemented with network accessible interfaces such as those described herein and illustrated in the Figures.

System Implementation

Figure 7:
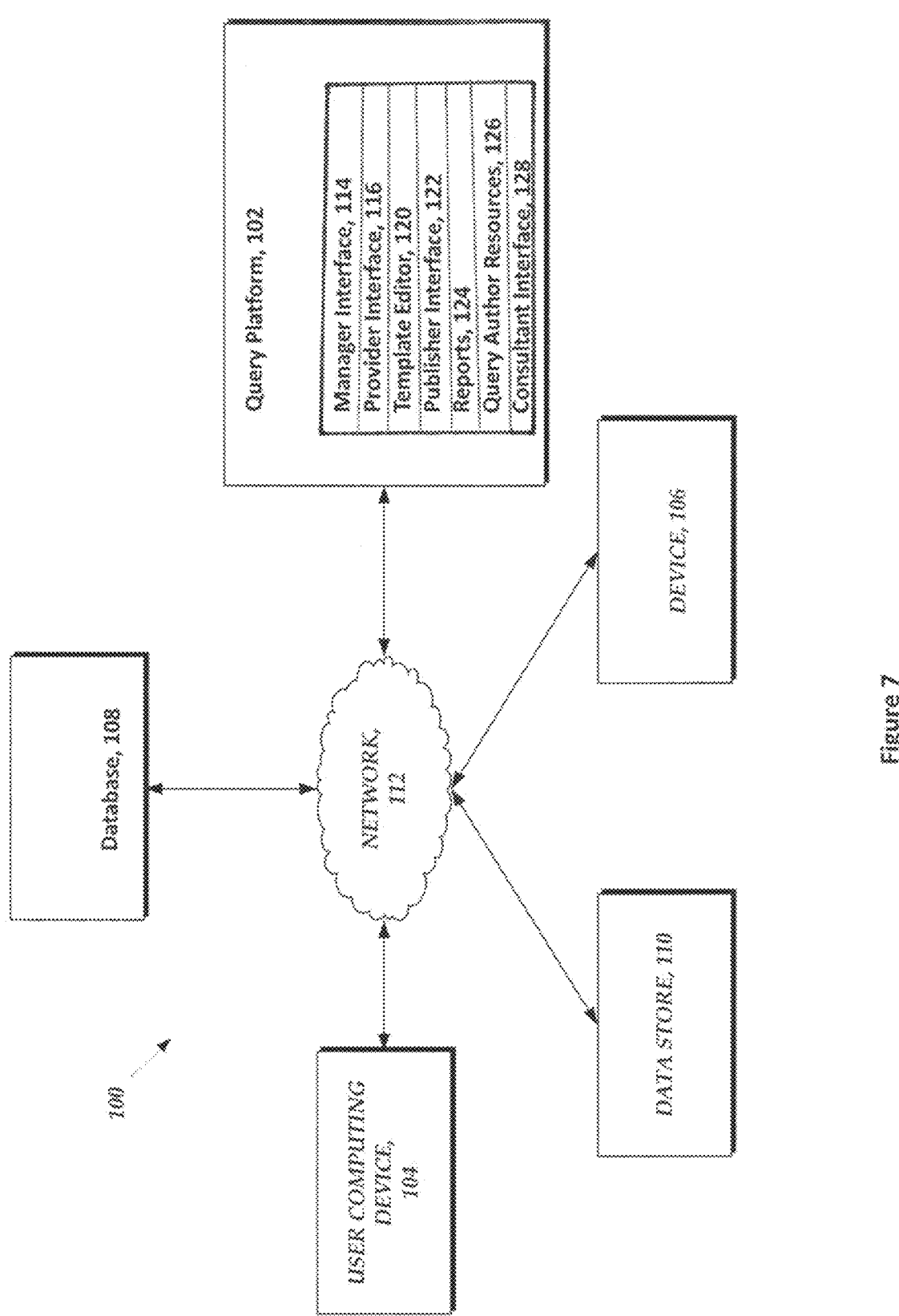
FIG. 7 is a block diagram illustrating the disclosed system and network environment of in accordance with the disclosure.

Referring to FIG. 7, which illustrates a block diagram of an embodiment of a computing environment of system 100 comprising query platform 102, in communication with one or more of a user computing device 104, a device 106, one or more a databases 108, or a data store 110 any of which may be interconnected via a private or public network 112.

In an illustrative embodiment, the user computing devices 104 or 106 may be one or more of a wide variety of computing devices including, but not limited to, personal computing devices, laptop computing devices, hand-held computing devices, terminal computing devices, mobile devices, wireless devices, various electronic devices and appliances and the like. The user computing device 104 may further be a stand-alone device.

The database 108 or data store 110 may be implemented with any storage device capable of maintaining data in storage. For clarity, a single data storage device 110 is illustrated in FIG. 1. However, it may be understood that the data store 110 may represent a plurality of data storage devices. Examples of the data storage device 110 may include, but are not limited to, static and dynamic memories, magnetic storage devices, solid state memory devices, and the like, implemented as part of the conventional computer system or within specialized database architecture.

One skilled in the relevant art will appreciate that the components and configurations provided in FIGS. 1 and 7 are illustrative in nature. Accordingly, additional or alternative components and/or configurations may be utilized without departing from the spirit and scope of the present disclosure. For example, any of the components of exemplary system 100 and network topology 112 can be implemented in digital electronic circuitry, in computer hardware, firmware, software and combinations thereof. The implementation can be as a computer program product. The implementation can, for example, be in a machine-readable storage device, for execution by, or to control the operation of, data processing apparatus. The implementation can, for example, be a programmable processor, a computer, and/or multiple computers.

Any of the functional modules described with reference to query platform 102 and any of the network accessible interfaces generated thereby may be implemented with one or more computer program applications which may execute on the same system or may execute remotely from each other but interact operably over network 112. Such computer programs may be implemented in any form of programming language, including compiled and/or interpreted languages, and the computer program can be deployed in any form, including as a stand-alone program or as a subroutine, element, and/or other unit suitable for use in a computing environment.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application specific integrated circuit). Subroutines and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include one or more clients and servers which may be remote from each other but operatively coupled through a communication network. The relationship of client and server arises by virtue of computer programs running on the respective computers and having a client-server relationship to each other.

The components of the illustrative system may be implemented on a circuit-switched or packet-switched network or hybrid combination thereof. Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, Bluetooth, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a worldwide web browser (e.g., Microsoft®. Internet Explorer®. available from Microsoft Corporation, Mozilla®. Firefox available from Mozilla Corporation). The mobile computing device includes, for example, a smartphone or tablet (e.g., iPhone®, iPad®, Android® device, Windows Phone®, etc.).

In light of the foregoing description and figures, the reader will appreciate that the disclosed system facilitates improvements in methods for query management and education, including the following benefits:

A consistent and standardized query review and response workflow on a mobile device that is easy and fast for clinicians and allows them to handle increasing query volume.

A collaborative approach to the query management process facilitated by a query activity feed that introduces full visibility into the query process and brings together all types of query authors associated with a provider organization (ex: clinical documentation specialists, medical coders, auditors, validators, quality staff, professional-fee billers) to coordinate on documentation-related queries and share knowledge resulting in greater operational efficiencies, less redundancy across all groups and less queries sent to clinicians.

Ensuring a more compliant query process by allowing provider organizations to purchase or create their own compliant query templates and share them across the organization so that all query authors participate in a standardized compliant approach to querying.

Delivering targeted provider clinical documentation improvement education along with queries on a mobile device in a clinician-friendly way by giving query authors the ability to compose, format, deliver, manage and track education to individual clinicians or groups of clinicians.

Using real-time graphical scorecards to inform users of individual query performance measures as compared to their group to drive higher response rates to queries within set deadlines and other important actions to a successful query process.

Providing greater insight into the query process by tracking all activity and giving users Reports that allow data to be accessed, manipulated and displayed so that the organization may leverage their data to refine and improve the query process.

Encouraging clinician accountability and greater motivation to respond to queries by humanizing the process with photographs and contact information of query authors displayed directly on queries and in other areas within the query platform 102.

As used in herein, the terms "comprise", "include", "and/or" are open ended and include the specified elements or steps and can include additional elements or steps, in any combinations with those described herein with components or steps not listed.

One skilled in the art will realize the disclosed system and methods may be embodied in other specific forms without departing from the spirit or essential characteristics thereof. The foregoing embodiments are therefore to be considered in all respects illustrative rather than limiting of the invention described herein, Scope of the invention is thus indicated by the appended claims, rather than by the foregoing description, and all changes that come within the meaning and range of equivalency of the claims are therefore intended to be embraced therein.

What is claimed is:

1. A system for distributed query management comprising:
    a network accessible memory for storing data associated with a plurality of patient records;
    a query management server comprising:
        a query platform configured to generate a first network accessible interface for authoring queries for clinicians and configured for receiving queries from a plurality of query authors, each of the queries identifying one of the plurality of patient records and including a query date, a request for a clinician to clarify a respective identified patient record, and a due date for the clinician to know when a response is required;
        the query platform configured to generate a second network accessible interface for clinicians to respond to queries; and
        wherein the second network accessible interface enables targeted educational content for the respective clinician to help reduce need for similar future queries to the respective clinician.

2. The system of claim 1, further comprising an executable publisher interface process configured to generate a network accessible publisher interface for displaying content and configured for enabling provider processes operatively coupled to the query management server over a network to upload content to the network accessible publisher interface.

3. The system of claim 1, wherein a query template is configured to store data comprising information not stored in the network accessible memory for storing data associated with a plurality of patient records.

4. The system of claim 1, wherein the plurality of patient records comprises data representing any of name, date of admission, date of discharge if available, date of birth, age, location, account number or billing number, medical record number, length of stay, days post discharge if available, and insurance company.

5. The system of claim 1 wherein a list of standard answers to an authored query is presented to a clinician as a list of possible answers.

6. The system of claim 1, wherein the second network accessible interface for clinicians to respond to queries is generated on a mobile device.

7. The system of claim 1, wherein the query management server further comprises an executable template editor configured to generate a network accessible user interface enabling query authors to select, create, store or categorize query templates useful in authoring queries.

8. A method for query management of patient information in a cloud-based network comprising:

providing a query management server operatively coupled to a network accessible memory for storing data associated with a plurality of patient records;

receiving at the query management server a query from one of a plurality of query authors, the query identifying one of the plurality of patient records and including a request for a clinician associated with the identified patient record to clarify the identified patient record;

transmitting via the query management server the received query to the clinician, including a link to targeted educational content for the respective clinician to help reduce need for similar future queries to the respective clinician; and receiving at the query management server a response from the clinician.

9. The method of claim 8, further comprising: enabling provider processes operatively coupled to the query management server over a network to upload content for display to a plurality of query author processes and query response processes.

10. The method of claim 8, wherein a query template may be configured to store data comprising any of a question, a list of possible answers, clinical information, query title, query instructions, provider education information, tags for reporting purposes, branding or footnote information.

11. The method of claim 8, wherein the plurality of patient records may comprise data representing any of name, date of admission, date of discharge if available, date of birth, age, location, account number or billing number, medical record number, length of stay, days post discharge if available, and insurance company.

12. The method of claim 8, further comprising generating graphical scorecards with an executable rating process, the graphical scorecards indicating performance measures of query response processes to query author processes.

13. The method of claim 8, wherein the query received by the clinician is received on a mobile device.

14. The method of claim 8, further comprising maintaining a plurality of query templates in memory accessible by the query management server and enabling a query author to perform any of select, modify, store or categorize one of the plurality of query templates.

15. A computer program product for use with a computer processor comprising a non-transient computer usable medium containing computer usable instructions embodied thereon for performing a method for query management of patient information comprising:

providing a query management server operatively coupled to a network accessible memory for storing data associated with a plurality of patient records;

receiving at the query management server a query from one of a plurality of query authors, the query identifying one of the plurality of patient records and including a request for a clinician associated with the identified patient record to clarify the identified patient record;

transmitting via the query management server the received query to the clinician, including a link to targeted educational content for the respective clinician to help reduce need for similar future queries to the respective clinician; and receiving at the query management server a response from the clinician.

16. The computer program product of claim 15, further comprising enabling provider processes operatively coupled to the query management server over a network to upload content for display to a plurality of query author processes and query response processes.

17. The computer program product of claim 15, wherein the plurality of patient records may comprise data representing any of name, date of admission, date of discharge if available, date of birth, age, location, account number or billing number, medical record number, length of stay, days post discharge if available, and insurance company.

18. The computer program product of claim 15, wherein the query received by the clinician is received on a mobile device.

19. The computer program product of claim 15, further comprising generating graphical scorecards with an executable rating process, the graphical scorecards indicating performance measures of query response processes to query author processes.

20. The computer program product of claim 15, further comprising maintaining a plurality of query templates in memory accessible by the query management server and enabling a query author to perform any of select, modify, store or categorize one of the plurality of query templates.

\* \* \* \* \*